United States Patent

Takesako et al.

[11] Patent Number: 5,260,214
[45] Date of Patent: Nov. 9, 1993

[54] AUREOBASIDIUM PULLULANS WHICH PRODUCES ANTIBIOTIC R106

[75] Inventors: Kazutoh Takesako, Kusatsu; Katsushige Ikai, Shiga; Kazuo Shimanaka, Tokyo; Junko Yamamoto, Moriyama; Fumiyo Haruna, Kyoto; Teruya Nakamura, Kusatsu; Hideyo Yamaguchi, Kawasaki; Katsuhisa Uchida, Tokyo, all of Japan

[73] Assignee: Takara Shuzo Co., Kyoto, Japan

[21] Appl. No.: 860,019

[22] Filed: Mar. 30, 1992

Related U.S. Application Data

[62] Division of Ser. No. 657,811, Feb. 2, 1991, Pat. No. 5,158,876, which is a division of Ser. No. 379,629, Jul. 13, 1989, Pat. No. 5,057,493.

[30] Foreign Application Priority Data

Jul. 19, 1988 [JP] Japan .................. 63-180095
Feb. 16, 1989 [JP] Japan .................. 1-36736
Jun. 19, 1989 [JP] Japan .................. 1-158112

[51] Int. Cl.$^5$ ............................. C12N 1/14
[52] U.S. Cl. .................. 435/254.1; 435/71.1; 435/171; 435/911
[58] Field of Search ............. 435/252.1, 71.3, 254, 435/71.1, 171, 911

[56] References Cited

U.S. PATENT DOCUMENTS

| | | | |
|---|---|---|---|
| 3,320,136 | 5/1967 | Zajic | 195/31 |
| 3,827,937 | 8/1974 | Kato et al. | 195/31 P |
| 4,004,977 | 1/1977 | Kato et al. | 195/31 P |
| 4,294,754 | 10/1981 | Takahara et al. | 260/112.5 R |
| 4,342,751 | 8/1982 | Moore et al. | 424/177 |
| 4,409,210 | 10/1983 | Kawaguchi et al. | 414/177 |
| 4,414,328 | 11/1983 | Imanaka et al. | 435/47 |
| 4,939,091 | 7/1990 | Sasaki et al. | 435/158 |
| 4,965,347 | 10/1990 | Misaki et al. | 536/1.1 |
| 5,019,514 | 5/1991 | Bock et al. | 435/254 |

FOREIGN PATENT DOCUMENTS 63565 4/1981 Australia .

OTHER PUBLICATIONS

ATCC Catalogue of Fungi/Yeasts, 15th Edition 1987.

*Primary Examiner*—Marian C. Knode
*Attorney, Agent, or Firm*—Wenderoth, Lind & Ponack

[57] ABSTRACT

An antibiotic R106 represented by the general formula I):

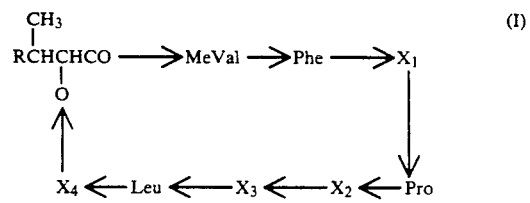

wherein:
R is methyl or ethyl;
$X_1$ is MePhe, β-HOMePhe or Phe;
$X_2$ is allo-Ile, Val or Leu;
$X_3$ is MeVal or Val;
$X_4$ is β-HOMeVal, γ-HOMeVal, MeVal, Val, N,β-MeAsp, β-HOMePhe, MePhe, MeDH$_{2,3}$Val or MeDH$_{3,4}$Val is produced by a process which comprises culturing a strain of the genus Aureobasidium that is capable of producing the said antibiotic R106 and collecting the said antibiotic from the fermentation broth. The antibiotic R106 compounds are useful in the treatment of fungal infection.

1 Claim, 2 Drawing Sheets

AUREOBASIDIUM PULLULANS WHICH PRODUCES ANTIBIOTIC R106

This application is a division of application Ser. No. 07/657,811 filed Feb. 2, 1991, (now U.S. Pat. No. 5,158,876) which is a division of application Ser. No. 379,629, filed Jul. 13, 1989, now U.S. Pat. No. 5,057,493.

The present invention relates to novel antibiotics R106 which are useful as therapeutic agents for the treatment of fungal infection. and a process for producing the same as well as for the use thereof.

As therapeutic agents for the treatment of fungal infection, there are known approximately 20 antibiotics including amphotericin B, nystatin, trichomycin, griseofulvin, pyrrolnitrin, clotrimazole, miconazole nitrate, etc. However, these antibiotics are questionable in activity and toxicity.

An object of the present invention is to provide novel antibiotics which have a high activity but low toxicity as therapeutic agents for treating fungal infection.

The present inventors isolated a number of microorganisms from the surface of plant leaves or from the soil, for purposes to discover novel antibiotics, purified antibiotics produced by these microorganisms and examined the biological properties of these antibiotics. As a result. It has been found that a series of antibiotics showing an antimicrobial activity against pathogenic fungi such as *Candida albicans, Cryptococcus neoformans*, etc. can be produced in fermentation broth of microorganisms belonging to the genus Aureobasidium.

These antibiotics have been isolated from the fermentation. broth; and as the result of examination of physicochemical properties of the antibiotics, it has been confirmed that these antibiotics are novel compounds that are not found in the literature. These antibiotics have been named R106. Thus, the present invention provides antibiotics R106 having the following structural formula and a process for production thereof as well as application thereof:

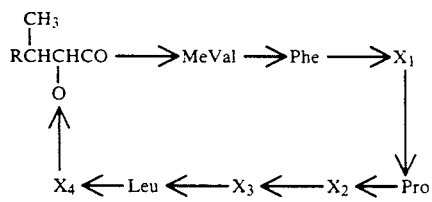

wherein:

R is methyl or ethyl;

$X_1$ is MePhe, $\beta$-HOMePhe or Phe;

$X_2$ is allo-Ile, Val or Leu;

$X_3$ is MeVal or Val;

$X_4$ is $\beta$-HOMeVal, $\gamma$-HOMeVal, MeVal, Val, N,$\beta$-MeAsp, $\beta$-HOMePhe. MePhe, MeDH$_{2,3}$Val or MeDH$_{3,4}$Val.

abbreviations for amino acids used in the above formula (I) are given in Table 9 later shown.

First, microorganisms used for the present invention can be a strain of the genus Aureobasidium which is capable of producing antibiotics R106 of the present invention represented by the general formula (I). An example of the microorganisms is Aureobasidium No. R106 (hereinafter this strain is referred to as strain No. R106), which the present inventors newly isolated from a soil sample collected at Kamitushima-cho, Kamiagata-gun, Nagasaki-ken, Japan. This strain is a new strain that has the characteristics described above and can produce advantageously novel antibiotics R106 of the present invention. Thus, this strain is one of the microorganisms which can be effectively used for the method of the present invention. Further, not only mutants of strain No. R106 which are prepared by natural or artificial mutation, but all microorganisms of the genus Aureobasidium which are capable of producing the antibiotics R106 of the present invention can be used for the method of the present invention.

Strain No. R106 has the following mycological characteristics.

(1) Growth on Various Nutrient Media

The following table shows cultural characteristics of strain No. R106 on various nutrient agar media after incubation for 4, 7, and 14 days at 25° C.

Strain No. R106 shows good growth on potato-dextrose agar, Czapek agar, and malt extract agar media. Colonies of the strain are usually mucoid, pasty, or rarely velvety, and then become leathery as time goes by. The colonies are white to creamy or light pink in color, then changing olive green to light brown or brown, sometimes finally to black with production of dark brown pigments, which is insoluble, as time goes by. Rhizoid-like structures are often formed around the colonies. Hyphae with a size of 2 to 15 µm in diameter elongate into the agar medium without forming aerial mycelia. Blastic conidia with a size of 1–5×2–10 µm, are often formed intercalary or terminal on hyphae like finger tips and sometimes form ball-like clusters. Vegetative cells in early stage of growth are yeast-like, and ellipsoidal or lemon-like in shape with a size of 3–5×-8–15 µm and multiply by polyblastic budding. The strain forms arthrospores with a size of 4–10×8–20 µm and chlamydospores with a size of 5–25×10–25 µm. No ascospores are observed.

| Media | Color of colonies after 4–7–14 days cultivation | Growth characteristics |
|---|---|---|
| Malt extract agar | Creamy-olive green–light brown | Good growth Chlamydospores are formed. |
| Potato dextrose agar | Creamy-olive green–light brown | Good growth *Blastic conidia* are abundant and form ball-like clusters. |
| Czapek agar | Creamy-brown-black | Good growth Hyphae are abundant, and often thick-walled. |
| Sabouraud agar | Creamy-olive green–dark green | Good growth Chlamydospores are observed. |
| Oatmeal agar | Creamy gray–light brown–dark brown | Moderate growth Hyphae are abundant. |
| YpSs agar | Creamy– light olive green–olive green | Good growth Hyphae are thin. *Blastic conidia* are abundant and form ball-like clusters. |

(2) Physiological Characteristics

1) Temperature range permitting growth
Temperature permitting growth: 12.5°–29.0° C.
Optimum temperature for growth: 23.0°–29.0° C.
2) Vitamin requirement
Growth in vitamin-free medium: Good growth.

3) Pigment formation

Insoluble dark brown pigments are produced. From the foregoing mycological characteristics, strain No. R106 is considered to belong to the genus Aureobasidium. Among the known species of Aureobasidium listed in W. B. Cooke, Mycopathologia et Mycologia Application, 17, 1–43 (1962)", J. A. von Arx, "The Genera of Fungi Sporulating in Pure Culture" J. Cramer, Lehre (1970), G. S. de Hoog & E. J. Hermanides-Nijhoff, Studies in Mycology, No. 15, p. 141–166, CBS, Baarn (1977) and other references, strain No. R106 is considered to be a member of *A. pullulans* from its characteristics. But known *A. pullulans* did not produce an antibiotic R106. So we designated the strain as *Aureobasidium pullulans* No. R106, and the strain was deposited on Jul. 8, 1988 at the Fermentation Research Institute, Agency of Industrial Science and Technology, Japan, under deposit number FERM BP-1938.

The antibiotics R106 of the present invention can be produced by inoculating and culturing the strain described above in a nutrient medium.

In culturing the R106-producing organisms, there may be appropriately used as carbon sources, for example, glucose, fructose, saccharose, starch, dextrin, glycerin, molasses, thick malt syrup, oils and fats, organic acids, etc.; as nitrogen sources, organic nitrogen compounds or inorganic nitrogen compounds such as soybean powder, cotton seed powder, corn steep liquor, casein, peptone, Casamino acids, yeast extract, meat extract, germ, urea, amino acids, ammonium salts, etc.; as salts, inorganic salts, for example, sodium salts, potassium salts, calcium salts, magnesium salts, phosphates, etc.: singly or in appropriate combination. If necessary and desired, heavy metals salts, e.g., iron salts, copper salts, zinc salts, cobalt salts, etc.; vitamins such as biotin, vitamin $B_1$, etc.; other organic or inorganic compounds which can assist growth of the producing organisms and accelerate production of R106, may be suitably added. Furthermore, defoaming agents or surface active agents such as silicone oil, polyalkylene glycol ethers, etc. may also added to the medium.

For culture, conventional techniques used for production of antibiotics by fermentation of microorganisms may be adopted, and liquid culture methods especially by shaking or tank fermentation with aeration and agitation are most suitable. Further by appropriately supplementing carbon sources, nitrogen sources, trace salts, etc. during the course of incubation, the amount of antibiotics R106 production can be increased. A preferred temperature for the culture is generally in a range of 15 to 30° C. A pH value for the culture is preferably in a range of 2 to 8. The number of days for fermentation may vary depending upon culture conditions but generally 1 to 14 days is sufficient.

The R106 thus accumulated in the fermentation broth can be advantageously collected therefrom by utilizing the physicochemical properties of the antibiotics.

That is, antibiotics R106 are contained in the fermentation broth and mycelial cake and can thus be obtained by extracting the whole fermentation broth with a hydrophobic organic solvent, for example, an organic solvent such as ethyl acetate, buryl acetate, chloroform, butanol, methyl isobutyl ketone, etc. Furthermore, antibiotics R106 can also be obtained after separation of tbe fermentation broth into the broth filtrate and mycelial cake by filtration or centrifugation. For isolation of R106 from the broth filtrate, the broth filtrate may be extracted with the aforesaid hydrophobic organic solvents. Alternatively, the broth filtrate may be brought into contact with an appropriate supporting resin to adsorb R106 in the filtrate thereto followed by elution with an appropriate solvent. For the purpose, supporting resins such as, for example, activated charcoal, cellulose powder, adsorptive resin, etc., which separate compounds according to their differences in the adsorbability to the resin, can be advantageously used. In order to elute antibiotics R106 from these resins aqueous solution of hydrophilic organic solvents, for example, aqueous acetone, aqueous alcohol, etc. can be used in appropriate combination, though the combination varies depending upon kind and property of the resin. Antibiotics R106 can be obtained from the mycelial cake by extracting with a hydrophilic organic solvent such as acetone or the like.

Crude R106 thus obtained can be further purified by conventional purification methods used for lipophilic antibiotics. An example of the methods is column chromatography with a supporting resin such as silica gel, activated aluminum, activated charcoal and adsorbtive resin.

In the silica-gel column chromatography antibiotics R106 can be eluted with chloroform, ethylacctylated, methanol, acetone, water, etc. which are used singly or in appropriate combination.

Isolation and purification by high performance liquid chromatography can also be advantageously utilized. Examples of the supporting resins which can be used include silica gel, silica gel with chemical bonds such as octadecyl, octyl or amino groups, or polystyrene type porous polymer gel, etc.

As a mobile phase, there may be used a mixed solvent of hexane, isopropyl alcohol and chloroform, etc., aqueous methanol or aqueous acetonitrile, etc.

Countercurrent chromatography which is a purification method based on differences of compounds in partition between two liquid phases can also be advantaqeously utilized. As the partition solvent system, there may be used a solvent mixture of hexaneethyl acetate-acetonitrile, chloroform-methanol-water or the like.

The physicochemical and biological properties of these new antibiotics R106 are as explained below by referring partly to the accompanying drawings wherein:

(1) Physicochemical Properties

Structures of antibiotics R106 obtained in accordance with the present invention are shown in Table 1.

TABLE 1

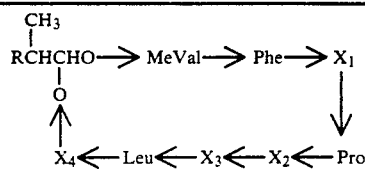

| Compound No. | R | $X_1$ | $X_2$ | $X_3$ | $X_4$ |
|---|---|---|---|---|---|
| 1 | $C_2H_5$ | MePhe | allo-Ile | MeVal | β-HOMeVal |

TABLE 1-continued $$\begin{array}{c}CH_3\\|\\RCHCHO \longrightarrow MeVal \longrightarrow Phe \longrightarrow X_1\\|\\O\\\uparrow \qquad\qquad\qquad\qquad \downarrow\\X_4 \longleftarrow Leu \longleftarrow X_3 \longleftarrow X_2 \longleftarrow Pro\end{array}$$

| Compound No. | R | $X_1$ | $X_2$ | $X_3$ | $X_4$ |
|---|---|---|---|---|---|
| 2 | $C_2H_5$ | MePhe | allo-Ile | MeVal | β-HOMeVal |
| 3 | $C_2H_5$ | MePhe | Val | MeVal | β-HOMeVal |
| 4 | $C_2H_5$ | MePhe | allo-Ile | MeVal | γ-HOMeVal |
| 5 | $C_2H_5$ | β-HoMePhe | allo-Ile | MeVal | β-HOMeVal |
| 6 | $C_2H_5$ | MePhe | allo-Ile | Val | β-HOMeVal |
| 7 | $C_2H_5$ | MePhe | allo-Ile | MeVal | MeVal |
| 8 | $C_2H_5$ | MePhe | allo-Ile | MeVal | Val |
| 9 | $C_2H_5$ | MePhe | Leu | MeVal | β-HOMeVal |
| 10 | $C_2H_5$ | MePhe | allo-Ile | MeVal | N,β-MeAsp |
| 11 | $CH_3$ | MePhe | allo-Ile | MeVal | MeVal |
| 12 | $C_2H_5$ | MePhe | Val | MeVal | MeVal |
| 13 | $C_2H_5$ | Phe | allo-Ile | MeVal | MeVal |
| 14 | $C_2H_5$ | MePhe | allo-Ile | MeVal | $MeDH_{3,4}Val$ |
| 15 | $C_2H_5$ | MePhe | allo-Ile | MeVal | β-HOMePhe |
| 16 | $C_2H_5$ | MePhe | allo-Ile | Val | MeVal |
| 17 | $C_2H_5$ | MePhe | allo-Ile | MeVal | MePhe |
| 18 | $C_2H_5$ | MePhe | allo-Ile | MeVal | $MeDH_{2,3}Val$ |

Abbreviations for the amino acids in Table 1 are indicated in Table 9 later presented.

Physicochemical properties of compound 1 are as follows.

(1) Molecular formula: $C_{60}H_{92}N_8O_{11}$ (2) Elemental analysis: C 65.0%, H 8.5%, N 9.9% (found) C 65.45%, H 8.36%, N 10.18% (calcd.)

(3) Melting point: 138°–140° C.

(4) Specific rotary power: $[\alpha]_D^{20} -254.3$ (C 1.0, methanol)

(5) Molecular weight: FAB-MS m/z 1101 (M+H), 1123 (M+Na)

Figure 1:
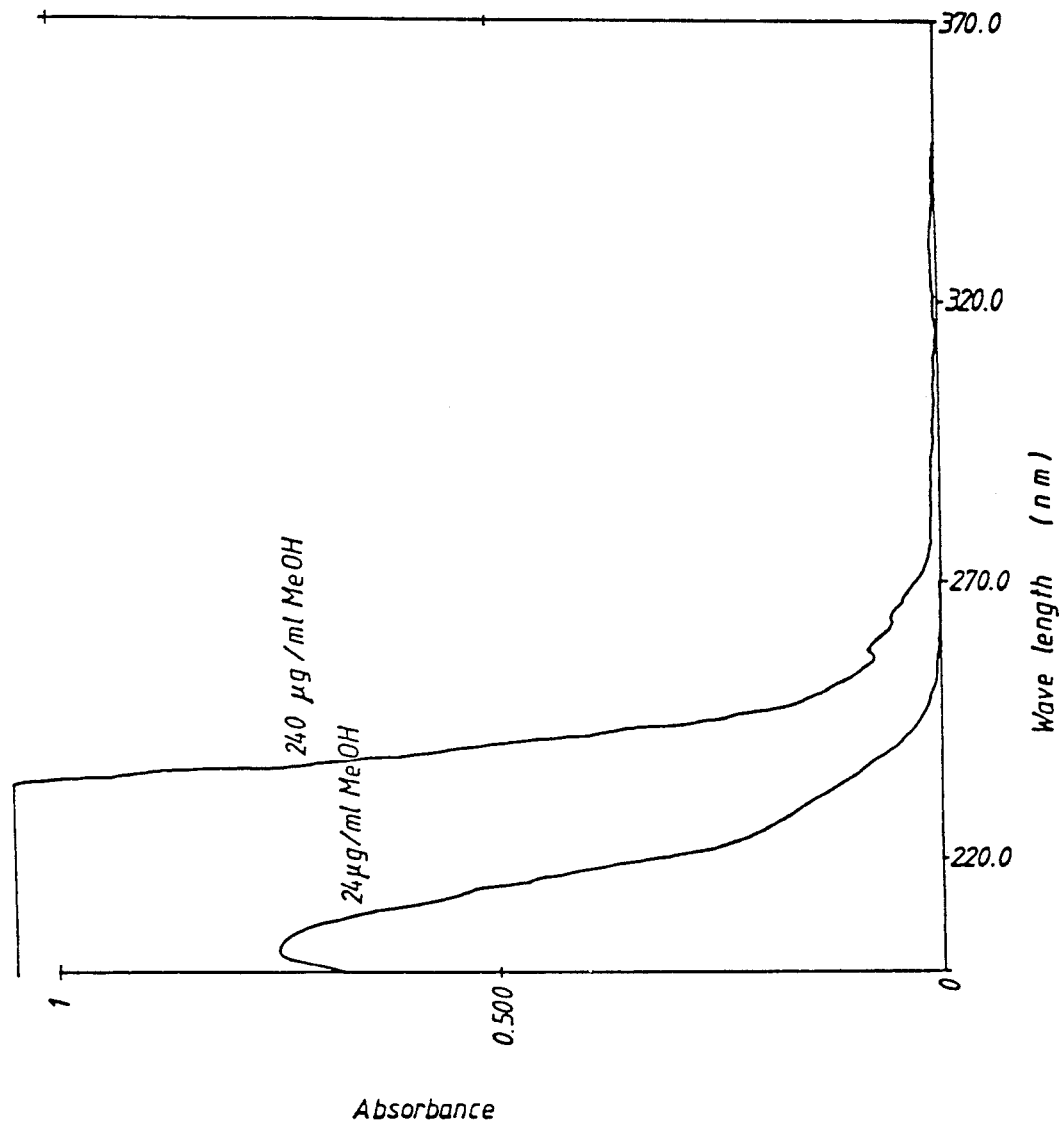
FIG. 1 is a graph showing the ultraviolet absorption spectrum of the compound 1.

(6) Ultraviolet absorption spectrum (in methanol): as shown in FIG. 1

Figure 2:
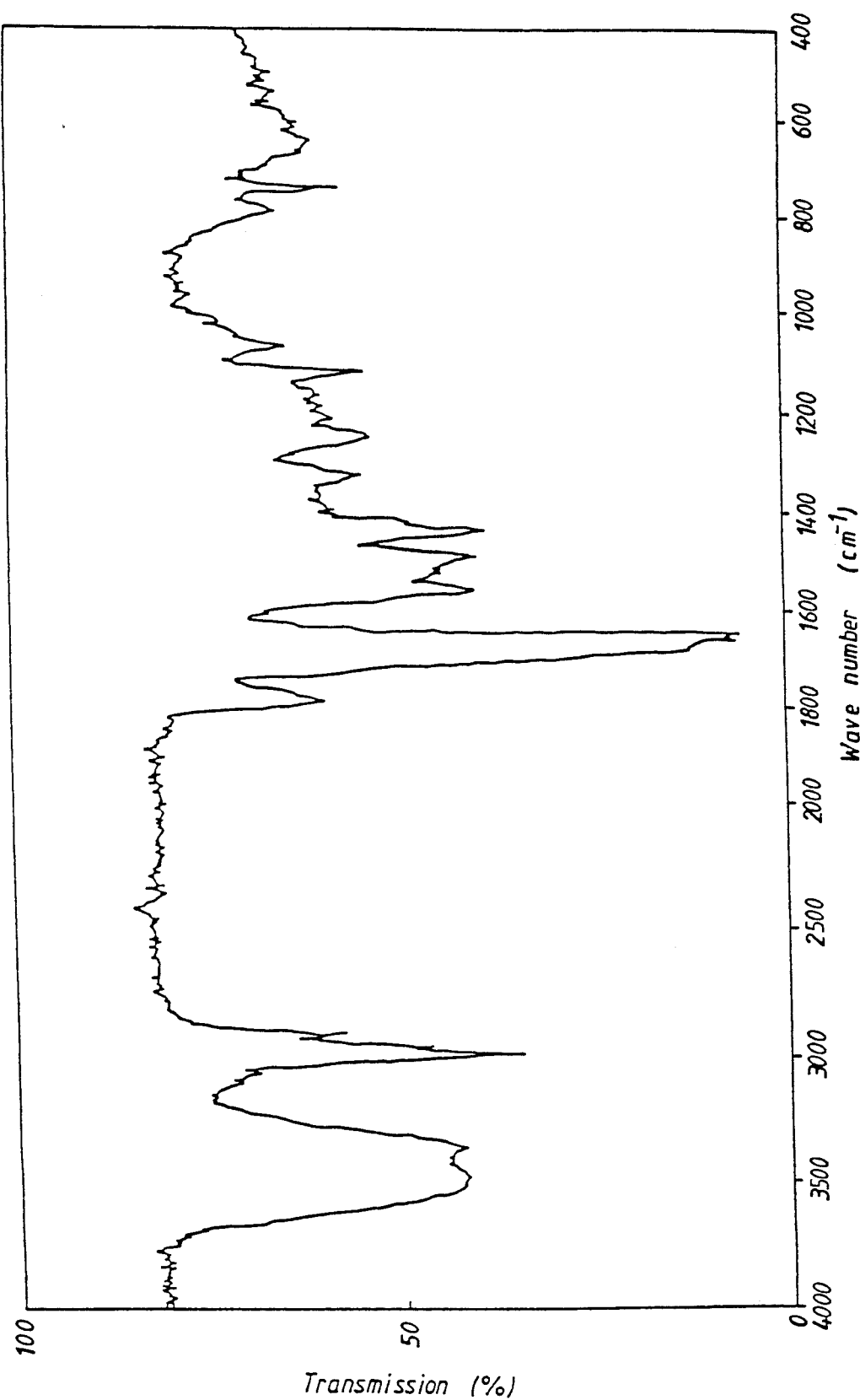
FIG. 2 is a graph showing the infrared absorption spectrum of the same compound.

(7) Infrared absorption spectrum (KBr method): as shown in FIG. 2

(8) Amino acid analysis: Proline, alloisoleucine, leucine and phenylalanine are detected (device: JCL-300 manufactured by JEOL Co., Ltd.; Detection: ninhydrin reaction)

(9) Color forming reaction: positive in 50% sulfuric acid and potassium permanganate and negative in ninhydrin and ferric chloride

(10) Solubility in solvent: soluble in chloroform, methanol, ethanol, N,N-dimethylformamide and dimethylsulfoxide; sparingly soluble in water

(11) Acidic, neutral or basic: neutral substance

(12) Color: white substance

Physicochemical properties of compounds 2 through 18 are shown in Table 2.

TABLE 2

| Compound No. | Elemental Analysis Found (%) C | H | N | Calcd. (%) C | H | N | Molecular Weight m/z (FAB-MS) | Molecular Formula | Specific Rotary Power $[\alpha]_D^{20}$ | Infrared Absorption cm$^{-1}$ (KBr method) | Amino Acid Analysis* |
|---|---|---|---|---|---|---|---|---|---|---|---|
| 2 | 64.81 | 8.53 | 10.06 | 65.17 | 8.34 | 10.30 | 1087 (M + H) 1109 (M + Na) | $C_{59}H_{90}N_8O_{11}$ | −222.3 (C1.0, methanol) | 3450, 3340, 2970, 1750, 1640, 1530, 1410, 1300, 1210, 1090, 700 | proline, alloisoleucine, leucine, phenylalanine |
| 3 | 65.09 | 8.61 | 9.96 | 65.17 | 8.34 | 10.30 | 1087 (M + H) 1109 (M + Na) | $C_{59}H_{90}N_8O_{11}$ | −345.0 (C0.30, methanol) | 3450, 3350, 2970, 1740, 1640, 1530, 1420, 1300, 1210, 1090, 700 | proline, valine, leucine, phenylalanine |
| 4 | 65.12 | 8.71 | 9.87 | 65.45 | 8.36 | 10.18 | 1101 (M + H) 1123 (M + Na) | $C_{60}H_{92}N_8O_{12}$ | −241.3 (C1.0, methanol) | 3450, 3350, 2970, 1740, 1640, 1540, 1420, 1300, 1200, 1090, 700 | proline, alloisoleucine, leucine, phenylalanine |
| 5 | 64.36 | 8.51 | 9.83 | 64.49 | 8.30 | 10.02 | 1117 (M + H) 1139 (M + Na) | $C_{60}H_{92}N_8O_{12}$ | −211.6 (C1.0, methanol) | 3450, 3340, 2970, 1740, 1640, 1530, 1420, 1300, 1210, 1080, 700 | proline, alloisoleucine, leucine, phenylalanine |
| 6 | 64.63 | 8.65 | 10.20 | 65.17 | 8.34 | 10.30 | 1087 (M + H) 1109 (M + Na) | $C_{59}H_{90}N_8O_{11}$ | −191.8 (C1.0, methanol) | 3470, 3330, 2980, 1740, 1640, 1530, 1410, 1290, 1220, 1090, 700 | proline, valine, alloisoleucine, leucine, phenylalanine |
| 7 | 66.25 | 8.69 | 10.31 | 66.39 | 8.54 | 10.32 | 1085 (M + H) 1107 (M + Na) | $C_{60}H_{92}N_8O_{10}$ | −248.1 (C1.0, methanol) | 3450, 3340, 2970, 1760, 1640, 1530, 1420, 1270, 1200, 1090, 700 | proline, alloisoleucine, leucine, phenylalanine |
| 8 | 65.87 | 8.60 | 10.34 | 66.14 | 8.47 | 10.46 | 1071 (M + H) 1093 (M + Na) | $C_{59}H_{90}N_8O_{10}$ | −170.0 (C0.80, methanol) | 3450, 3330, 2960, 1740, 1640, 1520, 1420, 1300, 1200, 1080, 700 | proline, valine, alloisoleucine, leucine, phenylalanine |
| 9 | 65.21 | 8.58 | 10.00 | 65.45 | 8.36 | 10.18 | 1101 (M + H) 1123 (M + Na) | $C_{60}H_{92}N_8O_{11}$ | −226.3 (C1.0, methanol) | 3500, 3320, 2990, 1750, 1640, 1520, 1420, 1300, 1200, 1090, 700 | proline, leucine, phenylalanine |
| 10 | 64.14 | 8.27 | 10.03 | 64.61 | 8.13 | 10.05 | 1115 (M + H) 1137 (M + Na) | $C_{60}H_{90}N_8O_{12}$ | −217.6 (C1.0, methanol) | 3450, 3320, 2970, 1740, 1640, 1540, 1420, 1300, 1200, 1080, 700 | proline, alloisoleucine, leucine, phenylalanine |
| 11 | 65.61 | 8.84 | 10.41 | 66.14 | 8.47 | 10.46 | 1071 (M + H) 1093 (M + Na) | $C_{59}H_{90}N_8O_{10}$ | −228.1 (C1.0, methanol) | 3450, 3340, 2970, 1740, 1640, 1530, 1420, 1300, 1200, 1090, 700 | proline, alloisoleucine, leucine, phenylalanine |
| 12 | 66.03 | 8.56 | 10.28 | 66.14 | 8.47 | 10.46 | 1071 (M + H) 1093 (M + Na) | $C_{59}H_{90}N_8O_{10}$ | −229.7 (C0.70, methanol) | 3450, 3320, 2970, 1740, 1640, 1530, 1420, 1300, 1200, 1090, 700 | proline, valine, leucine, phenylalanine |
| 13 | 65.82 | 8.52 | 10.16 | 66.14 | 8.47 | 10.46 | 1071 (M + H) 1093 (M + Na) | $C_{59}H_{90}N_8O_{10}$ | −210.0 (C0.31, methanol) | 3470, 3340, 2980, 1750, 1640, 1530, 1420, 1290, 1210, 1090, 700 | proline, alloisoleucine, leucine, phenylalanine |
| 14 | 66.50 | 8.49 | 10.12 | 66.52 | 8.37 | 10.34 | 1083 (M + H) 1105 (M + Na) | $C_{60}H_{90}N_8O_{10}$ | −205.1 (C1.0, methanol) | 3450, 3330, 2960, 1750, 1640, 1520, 1410, 1290, 1190, 1080, 700 | proline, alloisoleucine, leucine, phenylalanine |
| 15 | 66.58 | 8.37 | 9.73 | 66.87 | 8.07 | 9.75 | 1149 (M + H) 1171 (M + Na) | $C_{64}H_{92}N_8O_{11}$ | −256.7 (C1.0, methanol) | 3480, 3330, 2970, 1740, 1640, 1520, 1420, 1280, 1200, 1090, 700 | proline, alloisoleucine, leucine, phenylalanine |
| 16 | 65.94 | 8.58 | 10.29 | 66.14 | 8.47 | 10.46 | 1071 (M + H) 1093 (M + Na) | $C_{59}H_{90}N_8O_{10}$ | −215.4 (C0.44, methanol) | 3450, 3340, 2970, 1740, 1640, 1530, 1420, 1300, 1200, 1080, 700 | proline, valine, alloisoleucine, leucine, phenylalanine |
| 17 | 67.42 | 8.28 | 9.76 | 67.81 | 8.18 | 9.89 | 1133 (M + H) 1155 (M + Na) | $C_{64}H_{92}N_8O_{10}$ | −272.9 (C1.0, methanol) | 3460, 3350, 2980, 1750, 1640, 1530, 1420, 1280, 1220, 1090, 710 | proline, alloisoleucine, leucine, phenylalanine |
| 18 | 66.39 | 8.51 | 10.18 | 66.52 | 8.37 | 10.34 | 1083 (M + H) 1105 (M + Na) | $C_{60}H_{90}N_8O_{10}$ | −247.0 (C0.20, methanol) | 3460, 3330, 2970, 1740, 1640, 1530, 1410, 1300, 1220, 1100, 700 | proline, alloisoleucine, leucine, phenylalanine |

*Detected by ninhydrin reaction using JCL-300 manufactured by JEOL Co., Ltd.

(2) Biological Properties

The antibiotics R106 of the present invention are active against various fungi including pathogenic fungi. The minimum inhibitory concentration (MIC) of each antibiotic against various fungi was determined by the agar dilution method using casitone agar medium (2.0% glucose, 0.9% bacto-casitone, 1.0% yeast extract, 0.1% $KH_2PO_4$, 0.1% $Na_2HPO_4$, 1.0% sodium citrate, 2.0% agar: concentrations are all by w/v). The results determined with compound 1 are shown in Tables 3 and 4. The results determined with compounds 2 through 18 are shown in Table 5.

TABLE 3

| Strain | TIMM No. | Minimum Inhibitory Concentration (μg/ml) |
|---|---|---|
| Candida albicans | 0144 | 0.04≧ |
| Candida albicans | 1529 | 0.04≧ |
| Candida albicans | 1623 | 0.04≧ |
| Candida albicans var. stellatoidia | 1308 | 0.04≧ |
| Candida tropicalis | 0312 | 0.08 |
| Candida tropicalis | 0315 | 0.08 |
| Candida kefyr | 0298 | 0.16 |
| Candida parapsilosis | 0287 | 0.16 |
| Candida krusei | 0270 | 0.04≧ |
| Candida guilliermondii | 0257 | 0.08 |
| Candida glabrata | 1062 | 0.04≧ |
| Candida glabrata | 1064 | 0.08 |
| Cryptococcus neoformans | 0354 | 0.63 |
| Cryptococcus neoformans | 0355 | 0.31 |
| Cryptococcus neoformans | 0363 | 1.25 |
| Cryptococcus laurentii | 0352 | 0.31 |
| Cryptococcus terreus | 0424 | 0.31 |
| Rhodotorula rubra | 0923 | 0.63 |

Each minimum growth inhibitory concentration was determined after culturing at 27° C. for 4 days.

TABLE 4

| Strain | TIMM No. | Minimum Inhibitory Concentration (μg/ml) |
|---|---|---|
| Aspergillus clavatus | 0056 | 0.16 |
| Aspergillus flavus | 0058 | >80 |
| Aspergillus nidulans | 0112 | 0.16 |
| Aspergillus niger | 0113 | >80 |
| Aspergillus terreus | 0120 | 5 |
| Aspergillus citrinum | 1330 | >80 |
| Aspergillus commune | 1331 | 1.25 |
| Aspergillus crustorum | 1332 | >80 |
| Trichophyton mentagrophytes | 1177 | >80 |
| Trichophyton rubrum | 1216 | >80 |
| Microsporum canis | 0760 | >80 |
| Epidermophyton floccosum | 0431 | 2.5 |
| Fonsecaea pedrosoi | 0482 | 0.31 |
| Phialophora verrucosa | 0903 | >80 |
| Exophiala werneckii | 1334 | 1.25 |
| Cladosporium bantianum | 0343 | 0.63 |
| Cladosporium carrionii | 0337 | 1.25 |
| Sporothrix schenckii | 0959 | >80 |
| Histoplasma capsulatum | 0713 | 0.16 |
| Histoplasma capsulatum | 0714 | 0.08 |
| Paracoccidioides brasiliensis | 0878 | 80 |
| Paracoccidioides brasiliensis | 0880 | 0.31 |
| Geotrichum candidum | 0694 | 0.63 |
| Trichosporon cutanum | 1318 | >80 |
| Blastomyces dermatitidis | 1690 | 0.04≧ |
| Blastomyces dermatitidis | 0126 | 0.31 |

After culturing at 27° C. for 7 days, each minimum inhibitory concentration was determined.

TABLE 5

| Strain | TIMM No. | Compound No. 2 | 3 | 4 | 5 | 6 | 7 | 8 | 9 |
|---|---|---|---|---|---|---|---|---|---|
| Candida albicans | 0136 | 0.10 | 0.10 | 0.20 | 0.05≧ | 0.78 | 3.12 | 1.56 | 0.05≧ |
| Candida albicans | 0171 | 0.10 | 0.10 | 0.10 | 0.05≧ | 0.39 | 1.56 | 1.56 | 0.05≧ |
| Candida albicans | 1768 | 0.78 | 1.56 | 0.39 | 0.05≧ | 0.38 | 3.12 | 12.5 | 0.20 |
| Candida kefyr | 0301 | 0.20 | 0.20 | 0.78 | 0.20 | 0.38 | 25 | 25< | 0.20 |
| Candida glabrata | 1062 | 0.20 | 0.20 | 1.56 | 0.20 | 1.56 | 25< | 25< | 0.30 |
| Cryptococcus neoformans | 0354 | 1.56 | 1.56 | 25 | 3.12 | 25 | 25< | 25< | 25 |

| Strain | TIMM No. | Compound No. 10 | 11 | 12 | 13 | 14 | 15 | 16 | 17 | 18 |
|---|---|---|---|---|---|---|---|---|---|---|
| Candida albicans | 0136 | 0.78 | 1.56 | 6.25 | 6.25 | 1.56 | 12.5 | 3.12 | 12.5 | 6.25 |
| Candida albicans | 0171 | 0.78 | 1.56 | 6.25 | 12.5 | 1.56 | 25 | 1.56 | 25 | 3.12 |
| Candida albicans | 1768 | 12.5 | 1.56 | 25 | 12.5 | 12.5 | 25 | 25 | 25< | 25 |
| Candida kefyr | 0301 | 3.12 | 6.25 | 12.5 | 25 | 6.25 | 25< | 3.12 | 25< | 25 |
| Candida glabrata | 1062 | 3.12 | 25< | 25< | 25< | 12.5 | 25< | 25< | 25< | 25< |
| Cryptococcus neoformans | 0354 | 25 | 25< | 25< | 25< | 25< | 25 | 25< | 25< | 25< |

Antibiotics R106 exhibit a potent therapeutic effect on systemic candidiasis model of mice prepared by intravenous injection of Candida albicans, Candida albicans TIMM 1768 was cultured in Sabouraud-dextrose broth at 37° C. overnight, and the cells were collected and suspended in physiological saline. A cell suspension containing $1 \times 10^6$ cells was intravenously injected to ICR strain mice (5 week age, female). After 3 hours, a solution of an antibiotic R106 in TWEEN 80-ethanol-physioloqical saline (1 : 9 : 90, v/v) was subcutaneously, intravenously or orally given to the mice in various concentrations, and then once a day for 4 days the R106 drug solution was given. Mortality was assessed for 30 days after infection to determine the therapeutic effect. The results obtained by measurement with compound 1 are shown in Table 6.

TABLE 6

| Route | Dose (mg/kg) | Mean Survival Day | T/C (%) | Number of Animal Survived/ Number of Animal Tested |
|---|---|---|---|---|
| p.o. | 7 | 14.8 ± 4.8 | 121 | 0/5 |
|  | 14 | 23.2 ± 6.2 | 189 | 0/5 |
|  | 28 | 30.0 ± 0 | 245 | 5/5 |
| s.c. | 1.75 | 14.2 ± 2.9 | 116 | 0/5 |
|  | 3.5 | 18.8 ± 3.5 | 153 | 0/5 |
|  | 7 | 22.4 ± 7.0 | 183 | 2/5 |
|  | 14 | 27.2 ± 6.3 | 222 | 4/5 |
| i.v. | 0.875 | 14.6 ± 1.9 | 119 | 0/5 |
|  | 1.75 | 18.2 ± 5.0 | 149 | 0/5 |
|  | 3.5 | 19.2 ± 6.3 | 157 | 0/5 |
|  | 7 | 29.0 ± 2.2 | 237 | 4/5 |
|  | 14 | 26.6 ± 5.0 | 217 | 3/5 |
| Control | 0 | 12.3 ± 3.2 | 100 | 0/12 |

T/C is a value which expresses the mean survival day of the treated group to the mean survival day of the not treated control group by %.

All of the antibiotics R106 show low toxicity. The results of 50% lethal dose ($LD_{50}$) obtained when each of representative compounds of the present invention was given to mice intravenously, intraperitoneally and orally are shown in Table 7.

TABLE 7

| Compound No. | $LD_{50}$ (mg/kg) | | |
|---|---|---|---|
|  | i.v. | i.p. | p.o. |
| 1 | >200 | >400 | >1000 |
| 2 | >100 | >200 | >200 |
| 5 | >100 | >200 | >200 |
| 7 | >100 | >200 | >200 |
| 9 | >100 | >200 | >200 |

From the foregoing biological properties, it is evident that the antibiotics R106 are useful as therapeutic agents for various fungal infections such as candidiasis, histoplasmosis, blastmycosis, etc.

When the compound of the present invention is administered as a drug, the compound can be administered to animals including human as it is or as pharmaceutical compositions comprising, for example, 0.1 to 99.5%, preferably 0.5 to 90% of the compound in pharmaceutically acceptable non-toxic inert carrier.

As the carrier, solid, semisolid or liquid diluents, fillers and one or more of other aids for formulation can be used. The pharmaceutical composition is desirably administered in a single dose unit form. The pharmaceutical composition of the present invention can be administered orally, intratissularly, topically (percutaneously) or per rectum but, oral compositions and injections are preferred. Needless to say, the compound can be administered in preparations suited for these routes for administration.

It is desired that the dose as the antifungal agent be determined, taking into account conditions of the patient such as age, body weight, etc., route for administration, condition and degree of disease, etc. In general, it is proper to administer the compound of the present invention calculated as an effective ingredient in a range of 10 to 2000 mg per day. If the occasion demands, the dose may be smaller or larger than the above range. When a large dose is required, the dose may be desirably given portionwise several times a day.

Next, the present invention is described in more detail by referring to the examples below.

EXAMPLE 1

One platinum loop from a slant culture of strain No. R106 [deposited at the Fermentation Research Institute of the Agency of Industrial Science, & Technology under deposition No. 1938 (FERM BP-1938)] was inoculated in 100 ml of liquid medium (0.67% (w/v) Difco yeast nitrogen base, 2 % (w/v) glucose) in a 500 ml Erlenmeyer flask and shaken at 27° C for 2 days to give a seed culture. The seed culture, 1400 ml, was transferred into a 200-liter fermentor of containing 140 liters of the liquid medium described above followed by fermentation at 25° C. for 63 hours with aeration (100 liters/min.) and agitation (150 rpm). The fermentation broth was centrifuged to separate into the supernatant and the mycelial cake. To the mycelial cake was added 8 liters of acetone. After thoroughly mixing, acetone extract of mycelial cake was obtained. The acetone extract was concentrated under reduced pressure to give 81.5 g of the residue. Methanol was added to the residue to give an active extract. The methanol extract was condensed under reduced pressure to give 65.4 g of the residue. The resulting residue was subjected to a silica gel (made by Merck) column (9 cm×35 cm). The column was eluted with 7 liters of chloroform-methanol (49 : 1) to give the active fraction. The fraction was condensed under reduced pressure to give 10.6 g of the residue. The resulting residue was subjected to preparative high performance liquid chromatography column. PREPAK-500/$C_{18}$ (5.7 cm×30 cm) (manufactured by Waters), mobile phase: 70% (v/v) acetonitrile-water to give the active fraction. The fraction was condensed under reduced pressure to give 1.5 g of crude R106. The crude substance, 475 mg, was again subjected to preparative high performance liquid chromatography [column : CAPCELL Pak-500/$C_{18}$ (1 cm×25 cm) (manufactured by Shiseido Co., Ltd.), moving phase :70% (v/v) acetonitrile-water]to obtain the active fraction that shows the largesr peak in active fractions. The fraction was condensed under reduced pressure to give 370 mg of compound 1 as a white powder. The activity was determined by measuring an antifungal activity against Candida albicans TIMM 0136 according to the paper disk diffusion method using Casitone agar plate. Further the peak in high performance liquid chromatography was detected by measuring ultraviolet absorbance at 230 nm.

EXAMPLE 2

The seed culture, 1000 ml, of strain No. R106 prepared in a manner similar to Example 1, was inoculated in 100 liters of liquid medium (2% glucose, 0.5% ammonium sulfate, 0.15% $KH_2PO_4$, 0.05% $MgSO_4.7H_2O$, 0.01% $CaCl_2$, 0.01% NaCl (concentrations are all by w/v), 0.5 μg/ml $FeCl_2$, 0.5 μg/ml $ZnSO_4$) in a 200-liter fermentor followed by fermentation at 25° C. for 72 hours with aeration (100 liter/min) and agitation (100 rpm). To the culture was supplemented 20 liters of liquid medium (10% glucose, 2.5% ammonium sulfate, 5% polypeptone, 0.75% $KH_2PO_4$, 0.25% $MgSO_4.7H_2O$, 0.05% $CaCl_2$, 0.05% NaCl (concentrations are all by w/v), 2.5 μg/ml $FeCl_2$, 2.5 μg/ml $ZnSO_4$), and fermentation was further carried out at 25° C. for 65 hours with aeration (120 liters/min) and agitation (100 rpm).

The thus obtained fermentation broth was centrifuged to separate into the supernatant and the mycelial cake. To the obtained mycelial cake was added 10 liters of ethanol to extract R106. The ethanol extract was concentrated under reduced pressure to remove ethanol and the residue was extracted twice with 1 liter of ethyl acetate. The ethyl acetate extract was concentrated under reduced pressure to dryness, and the residue was dissolved in chloroform. The chloroform solution was subjected onto 1.5 liter of a silica gel column which had been previously saturated with hexane. After washing with 3 liters of hexane, the column was developed and eluted with 6 liters of hexane-isopropanol (7 : 3).

The active fraction was condensed under reduced pressure to give 15 g of the residue. The residue was dissolved in 100 ml of acetonitrile and the solution was divided into 30 and subjected to preparative high performance liquid chromatography [column : SOKEN PAK $C_{18}$ (5 cm×50 cm) (manufactured by Soken Chemical Co., Ltd.), mobile phase : 70% (v/v) acetonitrile-water]. The 18 active fractions eluted at the retention time shown in Table 8 were respectively collected and condensed under reduced pressure to give compounds 1 through 18 as white powders in amounts shown in Table 8. The activity detection and the peak detection of high performance liquid chromatography was carried out in the same manner as shown in Example 1.

TABLE 8

| Compound No. | Retention Time (min) | Yield (mg) |
|---|---|---|
| 1 | 67.0 | 3500 |
| 2 | 58.8 | 55 |
| 3 | 60.0 | 54 |
| 4 | 54.3 | 96 |
| 5 | 50.6 | 81 |
| 6 | 42.7 | 72 |
| 7 | 131.6 | 1380 |
| 8 | 72.5 | 32 |
| 9 | 62.2 | 60 |
| 10 | 44.5 | 12 |
| 11 | 111.4 | 76 |
| 12 | 112.6 | 60 |
| 13 | 109.8 | 24 |
| 14 | 91.6 | 107 |
| 15 | 90.4 | 42 |
| 16 | 75.0 | 78 |
| 17 | 146.7 | 18 |
| 18 | 102.2 | 15 |

TABLE 9

Val: valine
MeVal: N-methylvaline
β-HOMeVal: β-hydroxy-N-methylvaline

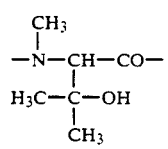

γ-HOMeVal: γ-hydroxy-N-methylvaline

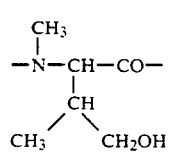

NeDH$_{2,3}$Val: N-methyl-2,3-didehydrovaline

TABLE 9-continued

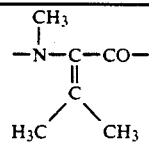

MeDH$_3$Val: N-methyl-3,4-didehydrovaline

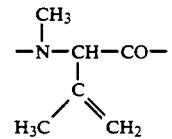

Phe: phenylalanine
MePhe: N-methylphenylalanine
β-HOMePhe: β-hydroxy-N-methylphenylalanine

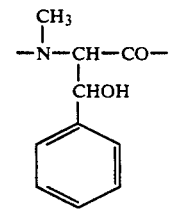

allo-Ile: alloisoleucine
Leu: leucine
Pro: proline
N,β-MeAsp: N,β-dimethylaspartic acid

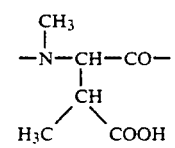

The antibiotics R106 of the present invention are novel antibiotics produced by the strains belonging to the genus Aureobasidium, have low toxicity and high antifungal activity against pathogenic fungi such as Candida albicans, Cryptococcus neoformans, etc. Therefore, the antibiotics are useful as clinical drugs, for example, therapeutic agents for the treatment of fungal infection.

What is claimed is:

1. A biologically pure culture capable of producing antibiotic R106 represented by formula (I) below, in a recoverable amount in an aqueous nutrient medium containing assimilable sources of carbon, nitrogen, and inorganic substances, having all the identifying characteristics of Aureobasidium pullulans FERM BP-1938 strain or a mutant thereof capable of producing antibiotic R106

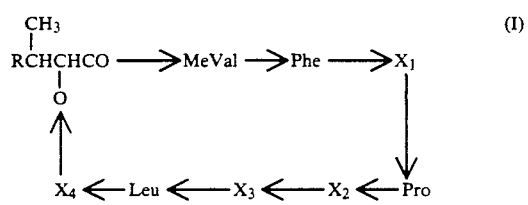 (I)

wherein:
R is methyl or ethyl;
$X_1$ is MePhe, β-HOMePhe or Phe;
$X_1$ is MePhe, β-HOMePhe or Phe;
$X_2$ is allo-Ile, Val or Leu;
$X_3$ is MeVal or Val;
$X_4$ is β-HOMeVal, γ-HOMeVal, MeVal, Val, N,β-MeAsp, β-HOMePhe, MePhe, MeDH$_{2,3}$Val or MeDH$_{3,4}$Val.

* * * * *